United States Patent
Myose et al.

(10) Patent No.: US 10,525,078 B2
(45) Date of Patent: *Jan. 7, 2020

(54) SOLID DIALYSIS A AGENT CONTAINING ALKALI METAL DIACETATE, AND TWO-PART TYPE LOW-ACETATE DIALYSIS AGENT USING SAME

(71) Applicant: Tomita Pharmaceutical Co., Ltd., Tokushima (JP)

(72) Inventors: Michiko Myose, Tokushima (JP); Hiroshi Noguchi, Tokushima (JP); Junya Kikuishi, Tokushima (JP); Hideyuki Aoyama, Tokushima (JP); Mina Hashimoto, Tokushima (JP); Yusuke Yoshimoto, Tokushima (JP)

(73) Assignee: Tomita Pharmaceutical Co., Ltd., Tokushima (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/026,798

(22) PCT Filed: Oct. 2, 2014

(86) PCT No.: PCT/JP2014/076372
§ 371 (c)(1),
(2) Date: Apr. 1, 2016

(87) PCT Pub. No.: WO2015/050188
PCT Pub. Date: Apr. 9, 2015

(65) Prior Publication Data
US 2016/0235785 A1 Aug. 18, 2016

(30) Foreign Application Priority Data
Oct. 2, 2013 (JP) .................................. 2013-207381

(51) Int. Cl.
| | | |
|---|---|---|
| *A61K 33/14* | (2006.01) | |
| *A61K 47/12* | (2006.01) | |
| *A61K 47/26* | (2006.01) | |
| *A61M 1/16* | (2006.01) | |
| *A61K 33/00* | (2006.01) | |

(52) U.S. Cl.
CPC .............. *A61K 33/14* (2013.01); *A61K 33/00* (2013.01); *A61K 47/12* (2013.01); *A61K 47/26* (2013.01); *A61M 1/1654* (2013.01)

(58) Field of Classification Search
CPC ......... A61K 33/14; A61K 47/12; A61K 47/26
See application file for complete search history.

(56) References Cited

U.S. PATENT DOCUMENTS

| | | |
|---|---|---|
| 4,655,941 A | 4/1987 | Suzuki |
| 4,756,838 A | 7/1988 | Veltman |
| 5,091,094 A | 2/1992 | Veech |
| 5,122,516 A | 6/1992 | Watanabe et al. |
| 5,252,213 A | 10/1993 | Ahmad et al. |
| 5,318,750 A | 6/1994 | Lascombes |
| 5,540,842 A | 7/1996 | Aoyama et al. |
| 5,616,248 A | 4/1997 | Schal |
| 6,309,673 B1 | 10/2001 | Duponchelle et al. |
| 6,399,110 B1 | 6/2002 | Kikuchi et al. |
| 6,428,706 B1 | 8/2002 | Rosenqvist et al. |
| 6,475,529 B2 | 11/2002 | Duponchelle et al. |
| 6,489,301 B1 * | 12/2002 | Kobira .................. A61K 9/167 514/23 |
| 2007/0231395 A1 | 10/2007 | Kai et al. |
| 2013/0168316 A1 | 7/2013 | Noguchi et al. |
| 2013/0189376 A1 * | 7/2013 | Carlsson .............. A61K 9/0029 424/678 |
| 2014/0097386 A1 | 4/2014 | Noguchi et al. |

FOREIGN PATENT DOCUMENTS

| | | |
|---|---|---|
| CN | 1448145 A | 10/2003 |
| CN | 1744884 A | 3/2006 |
| EP | 0 597 817 A2 | 11/1993 |
| JP | H06-245995 A | 9/1994 |
| JP | H07-024061 A | 1/1995 |
| JP | H07-059846 A | 3/1995 |
| JP | H10-087478 A | 4/1998 |
| JP | H10-259133 A | 9/1998 |
| JP | 2003-104869 A | 4/2003 |
| JP | 2007-130165 A | 5/2007 |
| JP | 4603977 B2 | 12/2010 |
| JP | 2013-150767 A | 8/2013 |
| JP | 2014-094928 A | 5/2014 |
| JP | 5517322 B1 | 6/2014 |
| WO | WO 94/016663 * | 8/1994 |
| WO | WO 99/09953 A1 | 3/1999 |
| WO | WO 2004/066977 A1 | 8/2004 |

(Continued)

OTHER PUBLICATIONS

Ito, JP 07-059846; published: Mar. 7, 1995, English machine translation assessed on Dec. 27, 2016.*

(Continued)

*Primary Examiner* — Michael G. Hartley
*Assistant Examiner* — Genevieve S Alley
(74) *Attorney, Agent, or Firm* — Knobbe, Martens, Olson & Bear LLP

(57) ABSTRACT

A solid dialysis A agent is provided, which is to be used in preparing a bicarbonate dialysis fluid, wherein: the solid dialysis A agent contains glucose, acetic acid and an acetate salt; at least a part of a mixture of the acetic acid with the acetate salt is an alkali metal diacetate; and the acetic acid/acetate salt molar ratio is adjusted to 1/0.5 to 1/2. This solid dialysis A agent makes it possible to prepare a bicarbonate dialysis fluid which has a total acetate ion concentration of 2 to less than 6 mEq/L. Further, the dialysis A agent exhibits excellent stability of ingredients and a reduced acetic acid odor.

16 Claims, No Drawings

(56) References Cited

FOREIGN PATENT DOCUMENTS

| | | |
|---|---|---|
| WO | WO 2005/094918 A1 | 10/2005 |
| WO | WO 2010/112570 A1 | 10/2010 |

OTHER PUBLICATIONS

Inoue et al. WO 94/016663; published: Aug. 1994; English machine translation assessed on Dec. 27, 2016.*

* cited by examiner

SOLID DIALYSIS A AGENT CONTAINING ALKALI METAL DIACETATE, AND TWO-PART TYPE LOW-ACETATE DIALYSIS AGENT USING SAME

TECHNICAL FIELD

The present invention relates to a solid dialysis agent A containing an alkali metal diacetate, and a low-acetate dialysis agent using the same. More specifically, the present invention relates to a solid dialysis agent A which is to be used for preparing a bicarbonate dialysis fluid together with a dialysis agent B containing sodium hydrogen carbonate, and which makes it possible to prepare a bicarbonate dialysis fluid having a total acetate ion concentration of less than 6 mEq/L, and is able to exhibit excellent stability of glucose and the like, and a reduced acetic acid odor. The present invention further relates to a dialysis agent containing the dialysis agent A

BACKGROUND ART

Dialysis therapy has been established as a treatment for patients with renal insufficiency, and performed for the purpose of controlling the concentration of blood electrolyte components, removal of uremic substances, correction of acid-base balance, or the like. The dialysis fluid used in the dialysis treatment includes a plurality of components, which should be combined at appropriate concentrations so as to satisfy objectives of treatment with less strain on the living body.

In recent years, bicarbonate dialysis fluids formed with use of sodium hydrogen carbonate for the correction of acid-base balance are popular, and it is also essential to combine an acid to make the dialysis fluid neutral. If these are distributed in the same container in which they coexist, such components generate carbon dioxide gas in the container and become very unstable, because of which, in general, two agents of agent A and agent B are produced as a dialysis agent to be mixed at the time of use for the preparation of the dialysis fluid.

Usually, the agent A contains sodium chloride, potassium chloride, calcium chloride, magnesium chloride, pH adjusting agent (acid and buffer ingredients as optional ingredients), and glucose, and the agent B contains sodium hydrogen carbonate. Moreover, in order to prevent the precipitation of insoluble salts, the formulation of calcium chloride and magnesium chloride into the agent B is contraindicated.

Conventionally, these agents A and B have been used as a liquid filled in a polyethylene container, but problems have arisen concerning transportation costs and poor operability in hospitals (weight, storage space, and disposal method of polyethylene container). As a result, today, a dialysis agent in powder form to be mixed with water before use has been put into practical use.

Although original dialysis agents in powder form are comprised of three agents including an agent A-1 containing a pH adjusting agent and an electrolyte, an A-2 agent consisting of only glucose, and an agent B consisting of sodium hydrogen carbonate, currently the two-pack type dialysis agents consisting of the agent A and the agent B are popular where the agent A-1 and the agent A-2 are combined.

Today, the bicarbonate dialysis agent is formulated so as to have the following composition and concentration when clinically used as a dialysis fluid.

TABLE 1

| | |
|---|---|
| $Na^+$ | 130~150 mEq/L |
| $K^+$ | 0~3.0 mEq/L |
| $Ca^{2+}$ | 2.0~4.0 mEq/L |
| $Mg^{2+}$ | 0~2.0 mEq/L |
| $Cl^-$ | 90~120 mEq/L |
| $HCO_3^-$ | 20~40 mEq/L |
| Acetic acid | 0~12 mEq/L |
| Citric acid | 0~3 mEq/L |
| Glucose | 0~250 mg/dL |

At the time of dialysis treatment, a liquid type agent A, or the agent A obtained by dissolving a powder type agent A, or the agent A obtained by dissolving powder type agents A-1 and A-2, and a liquid type agent B or the agent B obtained by dissolving a powder type agent B are diluted and mixed to be used as the dialysis fluid. However, as mentioned above, the bicarbonate dialysis fluid generates carbon dioxide gas as a result of coexistence of an acid and sodium hydrogen carbonate over time and the pH rises at the same time, so that an insoluble calcium carbonate and the like may be generated. This phenomenon raises such a problem that calcium concentration effective in the treatment is reduced and crystals are adhered to the tube or hose of the dialysis machine.

On the other hand, acetic acid has been used for a long time as a pH adjusting agent, but, in recent years, peripheral vasodilator action and cardiac inhibitory effect, induction of inflammatory cytokines, and strain on the patient with acetate intolerance, due to acetic acid have been questioned. That is, although acetic acid is metabolized in a short time and is not accumulated in the living body, it has a cardiac inhibitory effect, a peripheral vasodilator action, and, as a result, an action of reducing blood pressure. Since dialysis treatment is also a treatment for the removal of moisture in the body, a reduction in blood pressure due to moisture removal during and after dialysis would inevitably occur. The symptomatic treatment such as control of moisture removal and administration of vasopressors is often used in combination to prevent the reduction in blood pressure. The presence or absence of symptoms caused by these effects are different for each patient, and thus it is thought that such symptoms may also be attributed to the concentration of acetic acid contained in the dialysis fluid. In recent years, a dialysis method without acetic acid (an acetate free dialysis method) as one approach to overcome such a situation has been proposed.

Therefore, nowadays, those obtained by formulating citric acid in place of acetic acid as a pH adjusting agent are commercially available and have been clinically used (for example, see Patent Documents 1 to 4). However, there has been raised such a problem that because citric acid has a strong chelating action, a portion of the calcium in the dialysis fluid is chelated, thereby to decrease the ionized calcium concentration, and because citric acid is a stronger acid than acetic acid, the pH of the concentrated solution A lowers to cause a risk of corrosion of parts of a dissolution apparatus or a dialysis machine. If a large amount of organic acid salts are formulated in order to increase the pH of the solution A, crystals of calcium citrate are precipitated to affect the composition, which is also a problem. In other words, since citric acid is easy to form a chelate with an alkaline earth metal, it forms a chelate with calcium and magnesium in the dialysis fluid component. This action has a great effect on calcium in particular, and since control of the amount of calcium is very important in dialysis treatment, there is a drawback such that decrease of ionized calcium concentration due to such a chelate significantly affects the calcium balance in patients. For example, if the calcium and citric acid were included at almost the same concentration (ion equivalent ratio) in the dialysis fluid, about 35% of calcium is chelated to reduce the ionized calcium concentration in the dialysis fluid by a corresponding amount, resulting in a difficulty to control the blood calcium level. In addition, since citric acid also enters the body by dialysis, there is a risk such that citric acid binds to calcium in the blood to generate a poorly soluble calcium citrate, which is then deposited in the blood vessel. In addition, there is a concern such that it becomes difficult to control the calcium in the body, which is important for dialysis patients, because there is no explicit dynamics of the components such as citric acid and calcium after they enter the blood at the same time. Furthermore, there is a problem in the following points in that the decrease in ionized calcium concentration due to citric acid promotes the relaxation of cardiac muscle and vascular smooth muscle, leading to low blood pressure, and that citric acid is difficult to use in patients with bleeding tendency because it has an anticoagulant effect.

Further, citric acid is easy to handle in the normal handling because it is a solid, but since its concentrate is strongly acidic, hydrogen chloride gas is easily generated upon partial moisture absorption even if it is stored in powder form, which may cause a partial metal corrosion of the dissolution apparatus, resin deterioration, and the like. For example, Patent Document 1 describes a powder-type dialysis agent free from acetic acid, said dialysis agent being able to prevent the formation of insoluble compounds, suppress the precipitation of calcium carbonate, and inhibit the degradation of glucose by using a citric acid. These effects can be achieved by using citric acid within a limited range of pH 2.2 to 2.9. With such a pH range, there is a risk of corrosion of the dissolution apparatus and the dialysis machine, and the decrease in the ionized calcium concentration due to the strong chelation effect of citric acid may also affect the therapeutic effect as described above.

Therefore, it is not optimal to use citric acid as an acid other than acetic acid. Although organic acids other than citric acid which are safe for the living body, such as malic acid, lactic acid, fumaric acid, gluconic acid, etc. could be used, it is not clear about their behavior in the body after dialysis in chronic use and thus the amount of these acids should be reduced as much as possible, and it is also important to take into account the influence of these acid components on the dialysis fluid preparation apparatus and the dialysis machine.

On the other hand, as described above, it is concerned that citric acid etc. would decrease the ionized calcium concentration due to its strong chelating action, but, strictly speaking, acetic acid also reduces the ionized calcium concentration. The clinical problem of acetic acid has been neglected probably because acetic acid is metabolized fast, but, in practice, a dialysis fluid formed with use of acetic acid has a lower ionized calcium concentration than a dialysis fluid formed with use of hydrochloric acid as the pH adjusting agent, and the ionized calcium concentration is further reduced as the content of acetic acid is increased. Although not known in general, it is certain that a large content of acetic acid is a factor in lowering the ionized calcium concentration, but not as much as citric acid. From this point, it is clear that a less content of acetic acid is desirable.

All the dialysis agents A containing acetic acid which have been sold in Japan in the past have a total acetic acid content of 8 mEq/L or higher and a ratio of sodium acetate to acetic acid of 2.2 or more, regardless of whether the dialysis agent A is a liquid or a solid. Since the pH of the liquid A is 4.6 or more under this condition, there is such an advantage that the dialysis fluid preparation apparatus is less likely to be corroded and the dialysis fluid is easy to handle, in view of production of the liquid formulation.

The reason of the formulation of 8 mEq/L or higher of the total acetate content in Japan is because the past acetate dialysis agent (in which sodium acetate is formulated in 30 mEq/L or higher without using sodium bicarbonate) is changed to the bicarbonate dialysis agent so that benefits of bicarbonate and benefits of acetate can be brought about in combination, i.e., blood bicarbonate ions can be directly corrected whereas bicarbonate ions can be slowly corrected through the acetate metabolism.

On the other hand, liquid preparations (liquid A) are sold primarily outside of Japan. Sodium acetate is used as a part of the alkalizing agent in Japan, whereas only sodium hydrogen carbonate of the agent B is used as the alkalizing agent outside of Japan and sodium acetate is not used. Therefore, as an acetate ingredient, only acetic acid in an amount of 4 mEq/L or less has been used mainly as a pH adjusting agent.

However, when sodium acetate is not included in the dialysis liquid as described above, the pH of liquid A is 3 or less, resulting in adverse effects such as corrosion of the metal member of the dialysis fluid preparation apparatus and the dialysis machine, and strong irritation to the skin. In late years, a liquid A (including those prepared by dissolving an agent A powder) having a pH of 3 or less has been commercially available and the dialysis fluid preparation equipment manufacturers also deal with such a liquid A by employing parts made of acid resistant materials strongly resistant to corrosion. However, these materials are economically unfavorable because they are expensive.

In addition, the dialysis fluid containing acetic acid has a very strong and uncomfortable odor of acetic acid and thus, in the dialysis facilities where large quantities of dialysis fluid are handled, it is necessary to care the dialysis agent not to be placed in an open system as much as possible during its manufacturing or handling even though it is a liquid.

Next, in Japan, powder formulations of dialysis agents are popular as a result of a trend toward powdering of dialysis agents, and a large number of patents relating to bicarbonate dialysis agents that can be used in powder form have been disclosed. For example, Patent Document 5 describes that the manufacturing of the powder preparation becomes easier, when sodium acetate is combined to acetic acid in a ratio (molar ratio) of 1.56 to 3.29, preferably 2.49 to 3.29, in a powdery dialysis agent A because sodium acetate easily adsorbs acetic acid and is difficult to volatilize. However, even in the technique disclosed in Patent Document 5, the total acetate ion concentration of the finally prepared dialysis fluid is assumed to be 8 mEq/L or higher.

In addition, it is typical that sodium acetate is combined in an amount of from more than two times to five times, relative to acetic acid, and, for example, combination ratio of sodium acetate is 2.2 times (acetic acid 2.5 mEq/L: sodium acetate 5.5 mEq/L) for commercially available LYMPACK TA-1 in Japan, three times (acetic acid 2 mEq/L:sodium acetate 6 mEq/L) for KINDALY 2E, 4.5 times (acetic acid 2 mEq/L:sodium acetate 9 mEq/L) for HI-SOLV F, and 5 times (acetic acid 2 mEq/L: sodium acetate 10 mEq/L) for HI-SOLV D. Even apart from the transition of formulation in the past, the reason why the ratio of two times or less of sodium acetate to acetic acid has not yet been disclosed is because of a problem with acetic acid odor. In other words, as the ratio of sodium acetate is increased to three times, four times and so on, the acetic acid odor in powder preparation is reduced. In contrast, as the ratio of sodium acetate relative to acetic acid becomes close to double or becomes double or less, an excruciating odor of acetic acid occurs, because of which its practical use is not possible.

As seen from the above, even in Japan and abroad, there are only dialysis fluids containing acetic acid and having a total acetate ion concentration of 4 mEq/L or less, or 8 mEq/L or higher, and there has been no dialysis agent put to practical use, wherein the pH of the liquid A (concentrate) obtained by dissolving a solid agent A in water is set to about 4 and the total acetate ion concentration in the dialysis fluid is set to 4 to 8 mEq/L.

Only Patent Document 6 discloses that a preferable total acetate ion concentration is up to 5 mEq/L in the dialysis fluid containing acetic acid and sodium acetate. However, Patent Document 6 discloses a primary concentrate (sodium hydrogen carbonate, sodium chloride, and sodium acetate) and an individual concentrate (sodium, potassium, calcium, magnesium, hydrochloric acid/or acetic acid, glucose), and describes that the molar ratio of acetate/sodium in the final dialysis fluid obtained by combining the primary concentrate with the individual concentrate is 0.03 or less. That is, if the sodium content in the dialysis fluid is set to 140 mEq/L as typical cases, the total content of acetate ions in the dialysis fluid corresponds to 4.2 mEq/L or less. Further, Patent Document 6 describes that the sodium acetate to be combined with the primary concentrate is in an acetate/sodium ratio of less than 0.03, which indicates that the acetate ion content in the dialysis fluid is less than about 4 mEq/L. That is, Patent Document 6 discloses the embodiment of only a dialysis agent useful in the production of a dialysis fluid having a total acetate ion concentration of less than about 4 mEq/L.

In addition, according to Patent Document 6, the dialysis agent of Patent Document 6 enables individual patients to select various individual concentrates that can be provided, and the object of combining sodium acetate is to improve the stability and preserving property of the primary concentrate at low temperatures. In other words, a small amount of sodium acetate in the primary concentrate increases the solubility of sodium hydrogen carbonate and suppresses the formation of precipitates.

That is, since the dialysis agent of Patent Document 6 enables to perform the dialysis with various formulations according to the individual patients (calcium, magnesium, potassium, etc.) and requires a fairly complex system so that acetic acid and acetate salt are designed to be combined into different preparations, it differs from a general two-pack type dialysis agent comprising agent A and agent B in its dosage form and preparation method of the dialysis fluid. In addition, the technical means for reducing the acetic acid odor in the dialysis agent has not been studied at all in Patent Document 6. Further, in the dialysis agent of Patent Document 6, since the individual concentrate includes hydrochloric acid or acetic acid and does not include a basic ingredient, so that it will be exposed to a strong acidic condition of pH 3 or less, the dialysis agent of Patent Document 6 is not necessarily a good preparation in regard to corrosion problems of the dialysis fluid manufacturing apparatus, stability of glucose, and the like.

As described above, among general two-pack type dialysis agents that are widely used and contain the agent A (electrolytes, acids, glucose, etc.) and the agent B (sodium hydrogen carbonate) in combination, a dialysis agent having a total acetate ion concentration of 4 to 8 mEq/L does not exist, let alone any practical dialysis agent in powder form due to its strong acetic acid odor.

In fact, domestically and abroad, there is no successful example of any actual commercialization of dialysis agents in powder form, wherein the total acetate ion concentration has been set to less than 8 mEq/L in the dialysis fluid. This is probably because dialysis agents in powder form are difficult to commercialize as such dialysis agents poorly withstand clinical use in terms of fluidity and stability, and acetic acid odor. For example, acetic acid has a big influence on environment due to its pungent odor. Clinical dialysis fluid preparation is generally performed by a clinical engineer, but there is a problem of discomfort associated with pungent odor. Further, since acetic acid is also a factor in glucose degradation, a dialysis agent that is formulated with use of acetic acid and contains glucose is required to be formulated in sufficient consideration of the stability of glucose. Therefore, it is necessary to find the optimal formulation while sufficiently considering such problems.

In recent years, it has been reported at conferences and the like that a lower content of total acetate ion in a dialysis fluid is physiologically desirable and the total acetate ion are preferably less than 6 mEq/L or less than 4 mEq/L. Thus, there is an increasing demand for development of a dialysis agent that can be set to a lower total acetate ion concentration. It is believed that, by suppressing the total acetate ion concentration within a low range as described above, the onset of symptoms such as decrease in blood pressure can be suppressed almost without raising blood acetic acid concentration of the patient during dialysis, thereby to significantly improve safety, because the metabolic rate of acetic acid is faster than that of other organic acids and the content of acetic acid is less than that of conventional products. However, since a dialysis fluid having a low level of total acetate ion concentration, reported in the academic conferences, etc., is prepared by simply halving the amount of each of acetic acid and sodium acetate of the dialysis agent A that is set to the total acetate ion concentration of 8 mEq/L, there is a disadvantage that the pH of the dialysis fluid is inevitably high. In such a dialysis fluid with a high pH, its continuous use potentially causes vascular calcification of the patient, and there is also a problem of calcium deposition in the dialysis fluid preparation apparatus and the dialysis machine.

On the other hand, as a method for reducing the acetic acid odor as described above, there is disclosed a method of reducing the generated acetic acid odor by adding or spraying acetic acid to sodium acetate so that the acetic acid is adsorbed on the sodium acetate. There is also disclosed a method of mixing, as the dialysis component, sodium diacetate prepared in the same manner, or a method of forming sodium diacetate on the surface of the electrolyte component by adding acetic acid to an electrolyte component coated with sodium acetate (Patent Documents 5, 7 to 9). However, in any of these methods, sodium acetate relative to acetic acid is contained in an equivalent ratio of more than 2, and there is no description of the case with an equivalent ratio of 2 or less. Further, in these methods, labor in manufacturing, such as necessity for drying process under acetic acid atmosphere, is concerned. In addition, Patent Documents 8 and 9 disclose that sodium acetate is used in an equimolar or higher ratio to acetic acid, but a specific method in the case of using an equimolar amount of sodium acetate has not been described. In such a method, the condition of the equivalent ratio of substantially 3 or more, which is less likely to volatilize the acetic acid, is adopted. Moreover, even in these Patent Documents, the total acetate ion content in the dialysis fluid is not designed to be 4 to 8 mEq/L and these methods therein are not intended to disclose a formulation technique applicable to a low-acetate dialysis agent.

Based on the background of such a prior art, the development of a dialysis agent which allows for a low total acetate ion content in the dialysis fluid, exhibits excellent storage stability of glucose or the like and a reduced acetic acid odor, can suppress the corrosion of the dialysis fluid preparation apparatus and the dialysis machine, and can be put into practical use, as well as the development of a production method thereof has been desired.

PRIOR ART DOCUMENTS

Patent Documents

Patent Document 1: Japanese Patent Laid-open Publication No. 2003-104869
Patent Document 2: International Patent Application Publication No. WO 2005/094918
Patent Document 3: Japanese Patent Laid-open Publication No. 10-087478
Patent Document 4: International Patent Application Publication No. WO 2010/112570
Patent Document 5: Japanese Patent Laid-open Publication No. 7-24061
Patent Document 6: Japanese Patent Laid-open Publication No. 6-245995
Patent Document 7: Japanese Patent Laid-open Publication No. 2007-130165
Patent Document 8: Japanese Patent Laid-open Publication No. 7-59846
Patent Document 9: Japanese Patent Laid-open Publication No. 10-259133

SUMMARY OF THE INVENTION

Problems to be Solved by the Invention

An object of the present invention is to provide a solid dialysis agent A which allows for a low total acetate ion content in the dialysis fluid, exhibits excellent storage stability of glucose or the like and a reduced acetic acid odor, and is to be used for preparing a bicarbonate dialysis fluid, as well as to provide a low-acetate dialysis agent using the same.

Means for Solving the Problem

As the result of intensive and repeated studies to solve the above problems, the present inventors have found that if a solid dialysis agent A used for the preparation of a bicarbonate dialysis fluid includes acetic acid and acetate salt together with glucose therein wherein at least a part of a mixture of the acetic acid and acetate salt is an alkali metal diacetate and the molar ratio of acetic acid:acetate salt satisfies 1:0.5 to 2, it becomes possible to prepare a bicarbonate dialysis fluid having a total acetate ion concentration of 2 mEq/L or higher but less than 6 mEq/L, so that the acetic acid odor can be reduced in addition to the excellent stability of the components such as glucose and the like in the dialysis agent A. The present invention has been completed by further repeated studies on the basis of these findings.

That is, the present invention provides the invention with the following illustrative embodiments.

Item 1. A solid dialysis agent A which is to be used in the preparation of a bicarbonate dialysis fluid, wherein
the solid dialysis agent A contains glucose, acetic acid, and an acetate salt, and at least a part of a mixture of the acetic acid with the acetate salt is an alkali metal diacetate,
molar ratio of acetic acid:acetate salt is 1:0.5 to 2, and
the solid dialysis agent A is to be used for preparing a bicarbonate dialysis fluid having total acetate ions of 2 mEq/L or higher but less than 6 mEq/L.

Item 2. The dialysis agent A according to Item 1, wherein the alkali metal diacetate is sodium diacetate and/or potassium diacetate.

Item 3. The dialysis agent A according to Item 1 or 2, wherein the molar ratio of acetic acid:acetate salt is 1:1 to 1.5.

Item 4. The dialysis agent A according to any one of Items 1 to 3, which is to be used for preparing a dialysis fluid having total acetate ions of 2 mEq/L or higher but 5 mEq/L or less.

Item 5. The dialysis agent A according to any one of Items 1 to 4, wherein when the dialysis agent A is converted into a state of an aqueous solution that is concentrated to 35 times the concentration of each component in the finally prepared dialysis fluid, the pH of the solution is 3.9 to 4.6.

Item 6. The dialysis agent A according to any one of Items 1 to 5, wherein the acetate salt is sodium acetate.

Item 7. The dialysis agent A according to any one of Items 1 to 6, which further contains a physiologically available electrolyte other than sources for acetic acid and an acetate salt.

Item 8. The dialysis agent A according to Item 7, which contains sodium chloride, potassium chloride, magnesium chloride, and calcium chloride as an electrolyte.

Item 9. The dialysis agent A according to Item 8, wherein the magnesium chloride and/or calcium chloride is a dried product or an anhydride.

Item 10. The dialysis agent A according to any one of Items 7 to 9, which further contains as the electrolyte an organic acid salt other than the acetate salt, and/or contains as a pH adjusting agent an organic acid salt and/or an organic acid other than the acetic acid and acetate salt.

Item 11. The dialysis agent A according to any one of Items 1 to 10, wherein the alkali metal diacetate is obtained by the reaction of acetic acid with an alkali metal acetate, an alkali metal hydroxide, an alkali metal carbonate, or an alkali metal bicarbonate.

Item 12. The dialysis agent A according to any one of Items 1 to 11, which comprises:
a first material containing acetic acid and an acetate salt wherein at least a part of a mixture of the acetic acid and acetate salt is an alkali metal diacetate, and a second material containing a composition including a physiologically available electrolyte which is neither acetic acid nor acetate salt, wherein;
all of the acetic acid and acetate salt in the dialysis agent A are contained in the first material, or some of the acetic acid and acetate salt in the dialysis agent A are also contained in the second material, and
glucose is contained in the composition of the second material, and/or a third material containing glucose separately from the first material and the second material is included.

Item 13. The dialysis agent A according to any one of Items 1 to 12, wherein the moisture content is 1.1% by weight or less.

Item 14. The dialysis agent A according to any one of Items 1 to 13, wherein the moisture content is 1.0% by weight or less.

Item 15. The dialysis agent A according to any one of Items 1 to 14, which is accommodated in a packaging container of a water vapor transmission of 0.5 g/m$^2$24 h or less.

Item 16. The dialysis agent A according to any one of Items 1 to 15, which is accommodated in a packaging container together with a desiccant.

Item 17. A two-part type dialysis agent comprising the dialysis agent A according to any one of Items 1 to 16 and a dialysis agent B containing sodium hydrogen carbonate.

Item 18. A method for preparing a bicarbonate dialysis fluid, comprising the step of mixing the dialysis agent A according to any one of Items 1 to 16 and a dialysis agent B containing sodium hydrogen carbonate with water in such an amount that the bicarbonate dialysis fluid has total acetate ions of 2 mEq/L or higher but less than 6 mEq/L.

Item 19. Use of a composition for use in preparing a bicarbonate dialysis fluid having total acetate ions of 2 mEq/L or higher but less than 6 mEq/L, wherein the composition contains glucose, acetic acid, and an acetate salt, and at least a part of a mixture of the acetic acid with the acetate salt is an alkali metal diacetate, and molar ratio of acetic acid:acetate salt is 1:0.5 to 2.

Effects of the Invention

According to the dialysis agent A of the present invention, a bicarbonate dialysis fluid can be prepared so as to have a total acetate ion concentration of less than 6 mEq/L, and it is possible to suppress the onset of symptoms such as hypotension and the like and significantly improve safety during dialysis, as well as to effectively suppress the reduction of ionized calcium concentration in the dialysis fluid. In addition, the dialysis agent A of the present invention is improved in stability of other components such as glucose and the like and reduction of the acetic acid odor, and is less likely to corrode the dialysis fluid preparation apparatus and the dialysis machine so that the quality is improved and the improvement in a use environment is achieved in the medical practice, resulting in a marked improvement of handling in the medical practice.

Especially, in the dialysis agent A of the present invention, the pH of the liquid A (concentrate) obtained by dissolving a dialysis agent A in water can be adjusted to about 4.3 by setting the total acetate ion concentration in the dialysis fluid to 2 to 5 mEq/L and by setting the acetic acid:acetate salt molar ratio to 1:1 to 1.5, so that a bicarbonate dialysis agent that is clinically safer and more excellent in the stability during production and in qualitative stability can be provided.

Thus, according to the present invention, a bicarbonate dialysis fluid can be prepared so as to have a total acetate ion concentration of less than 6 mEq/L, and there can be provided a dialysis agent A that is clinically more useful and more excellent in the storage property and handling property than the conventional solid or liquid dialysis agent A.

In addition, according to the present invention, by providing a two-part type dialysis agent as a combination of the dialysis agent A and a dialysis agent B containing sodium hydrogen carbonate, it becomes possible to prepare a bicarbonate dialysis fluid so as to have a total acetate ion concentration of less than 6 mEq/L with excellent safety, quality, and operability without adversely affecting the dialysis fluid preparation apparatus and the dialysis machine.

MODE FOR CARRYING OUT THE INVENTION

As used herein, the indication "to" showing the numerical range means that it is equal to or more than the number at the left side and equal to or less than the number at the right side, and, for example, the numerical range of "X to Y" means "equal to or more than X and equal to or less than Y".

1. Dialysis Agent A

The dialysis agent A of the present invention is a solid dialysis agent A that is used in the preparation of a bicarbonate dialysis fluid, characterized by comprising glucose, acetic acid, and an acetate salt wherein at least a part of a mixture of the acetic acid and the acetate salt is an alkali metal diacetate and the molar ratio of acetic acid:acetate salt is 1:0.5 to 2, and by being used for the preparation of a dialysis fluid having total acetate ions of 2 mEq/L or higher but less than 6 mEq/L. The dialysis agent A of the present invention will be described in detail below.

<Acetic Acid and Acetate Salt>

The dialysis agent A of the present invention contains acetic acid and an acetate salt, and at least a part of a mixture of the acetic acid and acetate salt is in the form of an alkali metal diacetate. Thus, it is possible to effectively suppress the acetic acid odor by the fact that at least a part of a mixture of the acetic acid and acetate salt is an alkali metal diacetate. Note that the alkali metal diacetate is a complex (MH($C_2H_3O_2$)$_2$; M represents an alkali metal atom) formed from 1 mol of an alkali metal acetate and 1 mol of acetic acid, and thus 1 mol of the alkali metal diacetate supplies 1 mol of acetate salt (alkali metal acetate) and 1 mol of acetic acid.

Specific examples of the alkali metal diacetate used in the present invention include sodium diacetate, potassium diacetate, etc. These alkali metal diacetates may be used alone or in combination of two or more kinds thereof. Among the alkali metal diacetates, sodium diacetate is preferable.

Further, the dialysis agent A of the present invention may contain acetic acid and/or an acetate salt in the form other than the alkali metal diacetate as long as the acetic acid and acetate salt satisfy the molar ratio as described later. The acetic acid may be a glacial acetic acid. The acetate salt is not particularly limited as long as it is acceptable for the dialysis fluid, but includes, for example, sodium acetate, potassium acetate and the like. These acetate salts may be used alone or in combination of two or more kinds thereof. Note that these acetate salts may be anhydrous acetate salts.

In the dialysis agent A of the present invention, 1 mol of alkali metal diacetate is a complex consisting of 1 mol of acetic acid and 1 mol of alkali metal acetate. In other words, the proportion of the alkali metal diacetate to the total amount of the acetic acid and acetate salt is not particularly limited, but from the viewpoint of reducing the acetic acid odor more effectively, the amount of acetic acid and acetate salt derived from the alkali metal diacetate is 5 to 100 mol %, preferably 20 to 100 mol %, more preferably 50 to 100 mol % based on the total substance amount of acetic acid and acetate salt.

Here, when the total substance amount of the acetic acid and alkali metal acetate is defined as W mol in which the amount of the alkali metal diacetate is defined as X mol, the proportion of the acetic acid and acetate salt derived from the alkali metal diacetate in the total substance amount W is (2 X/W)×100 (mol %). For example, if 5 mol of the alkali metal diacetate is contained in 100 mol of the total substance amount of the acetic acid and acetate salt, 10 mol % of the total substance amount of the acetic acid and acetate salt is the acetic acid and acetate salt derived from the alkali metal diacetate.

The dialysis agent A of the present invention is set so as to satisfy the molar ratio of acetic acid:acetate salt of 1:0.5 to 2. By satisfying such molar ratio, the dialysis fluid can have a suitable pH due to the buffering action of the acetic acid-acetate salt even if the total acetate ion concentration in the dialysis fluid is set to less than 6 mEq/L. It is also possible to adjust the pH to about 3.9 to 4.6 in a liquid A (concentrate) obtained by dissolving a dialysis agent A in water, so that it becomes possible to suppress the corrosion of the dialysis fluid preparation apparatus and the dialysis machine. Furthermore, by satisfying such molar ratio, it becomes possible to increase the storage stability of glucose and the like in the dialysis agent A and further possible to reduce the acetic acid odor.

The molar ratio of acetic acid:acetate salt in the dialysis agent A of the present invention is preferably 1:0.75 to 1.75, more preferably 1:0.75 to 1.5, even more preferably 1:1 to 1.5, and especially preferably 1:1 to 1.25, from the viewpoint of exerting actions more effectively, including improvement of storage stability of glucose and reduction of acetic acid odor.

Here, as described above, since the alkali metal diacetate is a complex composed of 1 mol of acetic acid and 1 mol of alkali metal acetate, each of the acetic acid and acetate salt derived from 1 mol of alkali metal diacetate is calculated as 1 mol. That is, for example, in the case of a source for acetic acid and acetate salt which is derived only from the alkali metal diacetate, the molar ratio of acetic acid:acetate salt is 1:1. Also, for example, in the case of a source for acetic acid and acetate salt which is derived from X mol of alkali metal diacetate, Y mol of acetic acid, and Z mol of acetate salt, the acetic acid:acetate salt molar ratio is 1:(X+Z)/(X+Y).

With respect to the content of the source for acetic acid and acetate salt in the dialysis agent A of the present invention, it is set so as to satisfy a total acetate ion content in the finally prepared dialysis fluid, of 2 mEq/L or higher but less than 6 mEq/L, preferably 2 mEq/L or higher but less than 5.5 mEq/L, and more preferably 2 mEq/L or higher but less than 5 mEq/L. Thus, according to the dialysis agent A of the present invention, it is possible to set the total acetate ion content in the dialysis fluid to a lower level as well as a suitable pH of the dialysis fluid by virtue of the buffering action of the acetic acid-acetate salt, which has not been realized in the conventional two-part type dialysis agent, because of which onset of symptoms such as hypotension induced by acetate ions during dialysis can be suppressed, thereby making it possible to improve the safety remarkably.

<Glucose>

Glucose in addition to the above-mentioned acetic acid and acetate salt is included in the dialysis agent A of the present invention for the purpose of maintaining the blood glucose level of the patient. In the dialysis agent A of the present invention, degradation of glucose is suppressed by including the specified acetic acid and acetate salt in a specific ratio as mentioned above, so that an improvement in the glucose stability is achieved.

The content of glucose in the dialysis agent A of the present invention is appropriately set depending on the glucose concentration provided in the finally prepared dialysis fluid. Specifically, the content of glucose in the dialysis agent A is appropriately set so that the glucose concentration in the finally prepared dialysis fluid is 0 to 2.5 g/L, preferably 1.0 to 2.0 g/L.

<Other Components>

The dialysis agent A of the present invention may include physiologically available electrolytes used for dialysis fluid, in addition to acetic acid, acetate salt, and glucose mentioned above. Examples of such electrolytes include, for example, those that may be sources for magnesium ions, calcium ions, sodium ions, potassium ions, chloride ions, citrate ions, lactate ions, gluconate ions, succinate ions, malate ions, etc. It is desirable to include sources for at least sodium ions, chloride ions, magnesium ions, and calcium ions as the electrolytes (other than acetic acid and acetate salt) contained in the dialysis agent A of the present invention, and in addition to these sources, it is more desirable to further include a source for potassium ions.

Examples of a source for magnesium ions include magnesium salts. Examples of the magnesium salt used in the dialysis agent A include, but not particularly limited to, magnesium chloride, magnesium lactate, magnesium citrate, magnesium gluconate, magnesium succinate, magnesium malate, etc., as long as it is acceptable for the dialysis fluid. Among these magnesium salts, magnesium chloride is preferably used as a source for magnesium because its water solubility is high. These magnesium salts may be in the form of hydrates and/or dried products or anhydrides. Further, such magnesium salts may be used alone or in combination of two or more kinds thereof.

Examples of a source for calcium ions include calcium salts. Examples of the calcium salt used in the dialysis agent A include, but not particularly limited to, calcium chloride, calcium lactate, calcium citrate, calcium gluconate, calcium succinate, calcium malate, etc., as long as it is acceptable for the dialysis fluid. Among these calcium salts, calcium chloride is preferably used as a source for calcium because its water solubility is high. These calcium salts may be in the form of hydrates and/or dried products or anhydrides. Further, such calcium salts may be used alone or in combination of two or more kinds thereof.

Examples of a source for sodium ions include sodium salts. When sodium diacetate and/or sodium acetate is used as acetic acid and an acetate salt, the sodium diacetate and sodium acetate serve as a source for sodium ions. In addition, sodium ions may be supplemented by using also sodium salts other than sodium diacetate and sodium acetate so that a desired sodium ion concentration can be provided in the dialysis fluid. Examples of the sodium salt include, but not particularly limited to, sodium chloride, sodium lactate, sodium citrate, sodium gluconate, sodium succinate, sodium malate, etc., as long as it is acceptable for the dialysis fluid. Among these sodium salts, sodium chloride is preferably used as the sodium source, because sodium chloride is the most physiological substance. These sodium salts may be in the form of hydrates and/or dried products or anhydrides. Further, such sodium salts may be used alone or in combination of two or more kinds thereof.

Examples of a source for potassium ions include potassium salts. When potassium diacetate and/or potassium acetate is used as acetic acid and an acetate salt, the potassium diacetate and/or potassium acetate serve as a source for potassium ions, but potassium ions may be supplemented by using also potassium salts other than potassium diacetate and potassium acetate so that a desired potassium ion concentration can be provided in the dialysis fluid. The potassium salt includes, for example, but not particularly limited to, potassium chloride, potassium lactate, potassium citrate, potassium gluconate, potassium succinate, potassium malate, etc., as long as it is acceptable for the dialysis fluid. Among these potassium salts, potassium chloride is preferably used as the potassium source because the chloride ion is the most physiological substance. These potassium salts may be in the form of hydrates. Further, such potassium salts may be used alone or in combination of two or more kinds thereof.

Examples of a source for chloride ions include chloride salts. Examples of the chloride salt formulated in the dialysis agent A include, but not particularly limited to, sodium chloride, calcium chloride, magnesium chloride, potassium chloride, etc., as long as it is acceptable for the dialysis fluid. These chloride salts are preferably used because their water-solubility is high and they can achieve the role as the source for sodium, potassium, magnesium or potassium. These chloride salts may be in the form of hydrates and/or dried products or anhydrides. Further, such chloride salts may be used alone or in combination of two or more kinds thereof. In addition, hydrochloric acid that also serves as a pH adjusting agent can also be used as a source for chloride ions.

As described above, each electrolyte component to be incorporated into the dialysis agent A may be in the form of a hydrate, but preferably in the form of an anhydride from the viewpoint of more effectively reducing the acetic acid odor and improving the storage stability of glucose or the like.

The kind and the combination of the electrolyte components to be formulated in the dialysis agent A of the present invention are appropriately set according to the composition of ions to be contained in the finally prepared dialysis fluid, but preferred examples of the electrolyte component (neither acetic acid nor acetate salt) contained in the agent A include the combination of sodium chloride, magnesium chloride, calcium chloride, and potassium chloride. Further, when a combination of sodium chloride, magnesium chloride, calcium chloride, and potassium chloride is used as an electrolyte, it may further contain an organic acid salt (neither alkali metal diacetate nor acetate salt). Examples of such organic acid salt include sodium lactate, sodium gluconate, sodium citrate, sodium malate, sodium succinate, and the like. These organic acid salts may be used alone or in combination of two or more kinds thereof.

The content of each electrolyte contained in the agent A is appropriately set depending on each ion concentration provided in the finally prepared dialysis fluid. Specifically, in view of the kind and content of acetate salts and the amount of sodium bicarbonate formulated as the agent B, the content of the electrolyte components (neither acetic acid nor acetate salt) contained in the dialysis agent A is appropriately set in such a manner that the finally prepared dialysis fluid will satisfy each ion concentration as shown below in Table 2.

TABLE 2

| | Concentration in dialysis fluid |
|---|---|
| In the case of sodium ions | 120~150 mEq/L, preferably 135~145 mEq/L |
| In the case of potassium ions | 0.5~3 mEq/L, preferably 1.5~2.5 mEq/L |
| In the case of calcium ions | 1.5~4.5 mEq/L, preferably 2.5~3.5 mEq/L |
| In the case of magnesium ions | 0~2.0 mEq/L, preferably 0.5~1.5 mEq/L |
| In the case of citrate ions | 0~18 mEq/L, preferably 0~3 mEq/L |
| In the case of chloride ions | 90~135 mEq/L, preferably 100~120 mEq/L |
| In the case of lactate ions | 0~10 mEq/L |
| In the case of malate ions | 0~10 mEq/L |

TABLE 2-continued

| | Concentration in dialysis fluid |
|---|---|
| In the case of gluconate ions | 0~10 mEq/L |
| In the case of succinate ions | 0~10 mEq/L |
| In the case of bicarbonate ions | 20~40 mEq/L, preferably 25~35 mEq/L |

In addition, the above Table 2 shows each concentration of ions that include ions derived from acetate salts, and the amount of each electrolyte contained in the dialysis agent A of the present invention is also determined by taking into consideration the amount of each ion supplied from sources of the acetic acid and acetate salts. Further, the amount of the electrolyte (other than sodium diacetate and sodium acetate) serving as a source for sodium contained in the dialysis agent A of the present invention is determined so as to satisfy the sodium ion concentration shown in the above Table 2 described above, after taking into consideration the amount of sodium supplied from sodium hydrogen carbonate in the dialysis agent B and the amount of sodium supplied from sodium diacetate and/or sodium acetate when sodium diacetate and/or sodium acetate is used as the acetic acid and acetate salt.

For example, when the dialysis agent A of the present invention is formulated with use of acetic acid and sodium acetate at least a part of which is sodium diacetate, and other electrolytes, such as sodium chloride, potassium chloride, magnesium chloride, and calcium chloride, the proportion of sodium chloride is set to 13 to 65 mol, preferably 20 to 60 mol; potassium chloride to 0.08 to 1.5 mol, preferably to 0.3 to 1.25 mol; magnesium chloride to 0 to 0.5 mol, preferably 0.05 to 0.38 mol; and calcium chloride to 0.13 to 1.13 mol, preferably 0.25 to 0.88 mol, per 1 mol based on the total moles of acetic acid and sodium acetate, so that each ion concentration contained in the dialysis fluid satisfies the range shown in the above Table 1.

Since the molar ratio of acetic acid:acetate salt of the dialysis agent A of the present invention is set at a predetermined ratio, the pH of the finally prepared dialysis fluid is adjusted so as to have a reasonable range, but the dialysis fluid may separately contain a pH adjusting agent, if necessary. Examples of the pH adjusting agent that can be used in the dialysis agent A of the present invention include, but not particularly limited to, solid acids (e.g. citric acid, succinic acid, fumaric acid, malic acid, glucono delta-lactone, etc.), and their sodium, potassium, calcium, magnesium salts and the like, as long as it is acceptable for the dialysis fluid. Among these pH adjusting agents, an organic acid is preferably used. The pH adjusting agent may be used alone or in combination of two or more kinds thereof. Further, when such a pH adjusting agent is allowed to be included in the dialysis agent A of the present invention, the content thereof is appropriately set so that the pH of the liquid A that will be described later and is obtained by dissolving the dialysis agent A in water is satisfied and the pH of the dialysis fluid that is finally obtained is also satisfied.

<Dosage Form>

The dosage form of the dialysis agent A of the present invention is not particularly limited as long as it is a solid, but examples include powders, granules, and the like.

<pH>

The dialysis agent A of the present invention does not cause corrosion of the dialysis fluid preparation apparatus and the dialysis machine and ensure the safety in case of contact with the skin of workers in the clinical or manufacturing settings or of patients with dialysis at home, because acetic acid and acetate salt supplied from sources for acetic acid and acetate salt satisfy the above-mentioned ratio so that the pH of the liquid A obtained by dissolving the dialysis agent A in water is about 4.

As for the pH of the liquid A obtained by dissolving the dialysis agent A in water, more concretely, examples of the dialysis agent A include those that exhibit a pH of typically 3.9 to 4.6, preferably 3.9 to 4.5, and more preferably about 4.3 after made into an aqueous solution concentrated to 35 times the concentration of each component in the finally prepared dialysis fluid (hereinafter referred to as "35-fold concentrated agent A solution"). Here, the pH of the 35-fold concentrated agent A solution is a value measured at 25° C.

By satisfying the above-mentioned pH range with the dialysis agent A of the present invention, it is possible to ensure the stability of glucose. It is said that glucose is generally most stable around pH 3 (Shokuhin Seibun no Sougosayo (The Interaction between Food Ingredients), publisher: Shoichi NOMA, pages 5-15, editor: Mitsuo NAMIKI, Setsuro MATSUSHITA, issued May 1, 1980), and it has been confirmed that glucose is very stable in the pH range described above.

Further, by satisfying the above-mentioned pH range with the dialysis agent A of the present invention, it is also possible to effectively reduce the acetic acid odor. If the amount of the acetate salt in the dialysis agent A is less than 0.5 mol per 1 mol of acetic acid and the pH is lower than the above-mentioned pH range, the acetic acid odor tends to increase.

<Preferable Embodiments>

From the viewpoint of exerting more improved effects, such as storage stability, reduction in acetic acid odor, and suppression of corrosion of the dialysis fluid preparation apparatus and the dialysis machine, the dialysis agent A of the present invention is preferably one wherein the molar ratio of acetic acid:acetate salt is 1:0.5 to 2, the total acetate ions in the formation of the dialysis fluid are set to 2 mEq/L or higher but less than 6 mEq/L, and the pH of the 35-fold concentrated agent A solution is 3.9 to 4.6; more preferably one wherein the molar ratio of acetic acid:acetate salt is 1:0.75 to 1.5 (more preferably 1:1 to 1.5), the total acetate ions in the formation of the dialysis fluid are set to 2 mEq/L or higher but 5.5 mEq/L or less, and the pH of the 35-fold concentrated agent A solution is 4.1 to 4.4; and especially preferably one wherein the molar ratio of acetic acid:acetate salt is 1:1 to 1.25, the total acetate ions in the formation of a dialysis fluid are set to 2 mEq/L or higher but 5 mEq/L or less, and the pH of the 35-fold concentrated agent A solution is about 4.3.

<Moisture Content>

The moisture content of the dialysis agent A of the present invention is not particularly limited, and is appropriately set in view of storage stability, reduction of acetic acid odor, and the like. An example of the moisture content of dialysis agent A of the present invention is preferably 1.1% by weight or less, more preferably 1.0% by weight or less. It is possible to reduce the acetic acid odor more effectively and further improve the storage stability of glucose more effectively by reducing the moisture content to the range described above.

<Production Method and Packaging>

The production method of the dialysis agent A of the present invention is not particularly limited, but is appropriately set according to the dosage form, and a suitable production method will be described below.

Examples of a suitable production method of the dialysis agent A of the present invention include a production method comprising a first step of obtaining a first material containing acetic acid and acetate salt, at least a portion of which is an alkali metal diacetate, and a second step of mixing the first material with glucose and other components.

As the alkali metal diacetate used in the present invention, those produced by known methods may be used, or commercially available products may be used.

As a method for producing an alkali metal diacetate, there are known a method of reacting acetic acid with an alkali metal hydroxide, a method of reacting acetic acid with an alkali metal carbonate and/or an alkali metal bicarbonate, and the like. Note that the method of producing an alkali metal diacetate, herein exemplified, is merely illustrative and the alkali metal diacetate used in the present invention is not limited to those obtained by the method exemplified above. Usually, in order to suppress the volatilization of acetic acid and achieve the reduction of acetic acid odor, it is said that it is preferable to use sodium acetate in an equivalent ratio of 2 or more as much as possible relative to the acetic acid so as to take a form of adsorbing acetic acid on the sodium acetate or impregnating acetic acid into the sodium acetate. However, even if taking such a form, acetic acid is volatilized (desorption) as a result of absorbing moisture. That is, when produced or stored in a high humidity environment, the volatilization of acetic acid and the generation of acetic acid odor are more likely to occur. Such effect becomes larger as the equivalent ratio of sodium acetate to acetic acid becomes smaller.

The alkali metal diacetate contained in the dialysis agent A is subjected to the production of the first material in the first step. Furthermore, if the dialysis agent A contains acetic acid and/or acetate salt in the form other than alkali metal diacetate, these total amounts of acetic acid and/or acetate salt in the form other than alkali metal diacetate may be subjected to the preparation of the first material in the first step, or a portion of them may be subjected to the preparation of the first material in the first step, and the remainder may be mixed in the second step. Since acetic acid in the form other than the alkali metal diacetate is a cause of the acetic acid odor, it is preferable that a total amount of the acetic acid is contained in the form of alkali metal diacetate, and when the acetic acid in the form other than the alkali metal diacetate is contained, it is preferable to include such acetic acid in the first material.

The sodium diacetate, which has a low moisture content, emits the acetic acid odor only slightly in a low humidity environment, but tends to emit a strong acetic acid odor when the moisture content is large or in high humidity environments. In this regard, it is possible to suppress the acetic acid odor by lowering the moisture content of the first material obtained in the first step or by lowering the humidity during storage. For example, it becomes possible to obtain the first material with low acetic acid odor by preparing the first material under conditions of 60% RH or less, preferably 50% RH or less, and more preferably 40% RH or less (at 25° C. for all cases). In addition, the effect of suppressing the acetic acid odor can be further improved by using a means for removing excess moisture, such as heating to 30 to 90° C. in the preparation of the first material, blowing a dry air with low absolute humidity of, for example, 1.5 g/m$^3$ or less, or reducing the pressure, or by temporal storage or optional warming in a sealed container after the preparation of the first material.

In the second step, a solid agent A is prepared by mixing the first material obtained in the first step with glucose and other components. In the second step, the mixing of the first material obtained in the first step with other components may also be a simple mixing, or may be performed using wet granulation and dry granulation, such as agitating granulation, fluidized bed granulation, tumbling fluidized bed granulation, and pressure granulation, but a method without using water is preferable because the volatilization of acetic acid is increased by the presence of moisture.

In the second step, each of other components to be mixed may be mixed individually with the first material, or a composition comprising some or all of the other components to be mixed may be previously prepared and then the composition may be mixed with the first material. Preferably, there is exemplified a method wherein a composition containing an electrolyte (neither acetic acid nor acetate salt) and optionally acetic acid and an acetate salt (hereinafter also referred to as the second material) is previously prepared and then mixed with the first material. In the case of allowing an organic acid salt to be contained in the dialysis agent A of the present invention, the organic acid salt is preferably contained in the second material. Further, glucose may be contained in the second material, or may be mixed as a third material, with being separated from the first material and the second material, with the first material and the second material. In addition, some of glucose may be contained in the second material and the remainder may be mixed as a third material. Furthermore, in the case of mixing acetic acid (in the form other than alkali metal diacetate) in the second step, the acetic acid (in the form other than alkali metal diacetate) may be mixed with the second material, but may be mixed as a fourth material, with being separated from the first material, the second material and the optional third material. In addition, the organic acid other than acetic acid may be contained in at least one of the second material, the third material, and the fourth material, or may be mixed as a fifth material, with being separated from these materials.

Further, the composition subjected to the second step as the second material needs to be in the state of a mixture, and is preferably in the state of granules in view of moisture content. The method for producing a second material in the state of granules is not particularly limited, but examples include the following method. In the case of producing granules (second material) containing sodium chloride, potassium chloride, calcium chloride, and magnesium chloride as the electrolyte, an aqueous solution of calcium chloride and magnesium chloride is added to a mixture of sodium chloride and potassium chloride; the mixture is mixed under warming at 50 to 90° C.; optional other components (organic acid salts, glucose, etc.) are added thereto; and further mixing is performed under warming to form granules. Further, in the formation of the granules, calcium chloride and magnesium chloride in the form of powder may be added instead of adding an aqueous solution of calcium chloride and magnesium chloride, and a suitable amount of water may be added before or after the addition of such powdery calcium chloride and magnesium chloride. Note that the granules should be preferably dried thoroughly regardless of which granulation operation is employed. In addition, when the second material is used in the state of a mixture, anhydrous calcium chloride and anhydrous magnesium chloride are preferably used.

As a preferred embodiment of the second step, there is exemplified a method wherein a first material, a second material, an optional third material, an optional fourth material, and an optional fifth material are mixed under a low humidity condition (60% RH or less, preferably 50% RH or less, and more preferably 40% RH or less (at 25° C. in all cases)). At the time of mixing in the second step, an effect of suppressing the acetic acid odor can be more enhanced by using the means for removing the excess moisture, such as heating to 30 to 90° C., blowing of a dry air having a low absolute humidity, or pressure reduction. From the viewpoint of more reducing the acetic acid odor of the dialysis agent A to be produced, it is preferred that the first material, the second material, and the third material added as needed are in the state of low moisture content. Examples of such a method of reducing the moisture content in this way include a method comprising drying in advance each raw material to be supplied to the second step, at 90 to 140° C. and cooling the dried material by a cold air having an absolute humidity of 1.5 g/m$^3$ or less.

The dialysis agent A thus produced is optionally subjected to a drying treatment so as to have the moisture content described above, and is then provided as being accommodated in a packaging container. The packaging container used for packaging the dialysis agent A includes, for example, a flexible bag and a hard bottle. As the packaging container, it specifically includes silica vapor deposition laminated bag, aluminum vapor deposition laminated bag, aluminum oxide vapor deposition laminated bag, aluminum laminate bag, polyethylene hard bottle, and the like. Especially, a packaging bag formed with use of a metal foil such as an aluminum foil (aluminum laminated bag, etc.) can keep water vapor transmission at a low level and suppress more effectively acetic acid from being volatilized and moisture absorption from the environment. In addition, the water vapor transmission of these packaging containers is preferably 0.5 g/m$^2$·24 h (40° C., 90% RH) or less, and more preferably 0.2 g/m$^2$·24 h (40° C., 90% RH) or less from the viewpoint of reducing the acetic acid odor more effectively. The water vapor transmission is a value measured according to the measurement method specified in JIS Z0208 "Testing Methods for Determination of the Water Vapor Transmission Rate of Moisture-Proof Packaging Materials (Dish Method)".

Furthermore, in order to more effectively reduce moisture content of the dialysis agent A to be accommodated in the packaging container, a desiccant may be accommodated in the packaging container together with the dialysis agent A. The desiccant is not particularly limited, but includes, for example, zeolite, magnesium sulfate, sodium sulfate, silica gel, alumina, and the like. When the desiccant is accommodated in a packaging container, the desiccant may be combined into a part of the plastic (for example, polyethylene layers) constituting the container and such a container may be used, or a space (a separate room) to accommodate the desiccant in the packaging container may be provided. Further, the desiccant being in a state where it is placed in a nonwoven fabric so as not to mix with the solid agent A may be accommodated in a packaging container.

2. Dialysis Agent

The present invention further provides a two-part type dialysis agent comprising the dialysis agent A described above and a dialysis agent B containing sodium hydrogen carbonate.

No inclusion of electrolyte components other than sodium bicarbonate in the dialysis agent B used in the dialysis agent of the present invention is desirable and such components consisting substantially of only sodium bicarbonate are preferred.

Further, the dialysis agent B may be either solid or liquid form, but its solid form is preferable from the viewpoint of ease of transportation and storage.

If the dialysis agent B is a liquid, the content of sodium bicarbonate in the liquid dialysis agent B may be an amount capable of satisfying the desired bicarbonate ion concentration in the finally prepared dialysis fluid, but examples include 4 to 8 g/100 mL, preferably 6 to 8 g/100 mL.

In the dialysis agent of the present invention, the amount used of the dialysis agent B is preferably set so that a bicarbonate ion concentration in the finally prepared dialysis fluid is 25 to 35 mEq/L, in consideration of the ratio of acetic acid:sodium acetate in the dialysis agent A, the amount of total acetate ions, and the pH of the dialysis fluid. In particular, from the viewpoint of correction of acidosis of dialysis patients as well as control of the total alkali amount of the dialysis fluid to the appropriate range, a more preferable amount used of the dialysis agent B is such an amount that the bicarbonate ion concentration in the finally prepared dialysis fluid is 27 to 33 mEq/L.

The dialysis agent of the present invention is used to prepare a bicarbonate dialysis fluid. Specifically, a dialysis fluid is prepared by mixing a dialysis agent A with a dialysis agent B in a predetermined amount of water (preferably purified water), followed by dilution. In the preparation of the dialysis fluid using the dialysis agent of the present invention, the dialysis agent A is dissolved as needed in an appropriate amount of water to prepare a liquid A (a concentrate), which may be used in the preparation of a dialysis fluid. In addition, even if the dialysis agent B is a solid, the solid agent B may be dissolved as needed in an appropriate amount of water to prepare a liquid B (a concentrate), which may be mixed with the dialysis agent A and a predetermined amount of water.

Further, the pH of the dialysis fluid prepared by the dialysis agent of the present invention is not particularly limited as long as it satisfies the range that is acceptable as a dialysis fluid, but it is preferably 7.2 to 7.6, more preferably 7.3 to 7.5, especially preferably 7.3 to 7.4, in view of avoiding the risk of excessive correction of acidosis of dialysis patients. The dialysis agent A of the present invention is set to be able to prepare a dialysis fluid within the above pH range by the acetic acid/acetate salt sources satisfying a specific composition, in addition to the buffering action of bicarbonates.

EXAMPLES

Hereinafter, the present invention is specifically described by way of Examples. However, the present invention is not to be construed as being limited to the following Examples.

Test Example 1

(1) Preparation of Dialysis Agent A

Example 1

First, sodium chloride 11.15 kg, potassium chloride 0.261 kg, calcium chloride hydrate 0.386 kg, and magnesium chloride hydrate 0.178 kg were mixed under heating, and after further addition of water 0.178 kg, the mixture was granulated and dried at 130° C. to obtain an electrolyte composition. Then, the electrolyte composition 239.4 g, sodium diacetate 4.97 g, glacial acetic acid 2.10 g, and glucose 52.5 g were mixed with stirring to obtain a dialysis agent A. The molar ratio of acetic acid:sodium acetate in the obtained dialysis agent A is 1:0.5.

Example 2

First, sodium chloride 11.05 kg, potassium chloride 0.261 kg, calcium chloride hydrate 0.386 kg, and magnesium chloride hydrate 0.178 kg were mixed under heating, and after further addition of water 0.178 kg, the mixture was granulated and dried at 130° C. to obtain an electrolyte composition. Then, the electrolyte composition 237.4 g, sodium diacetate 9.95 g, and glucose 52.5 g were mixed with stirring to obtain a dialysis agent A. The molar ratio of acetic acid:sodium acetate in the obtained dialysis agent A is 1:1.

Example 3

First, sodium chloride 10.94 kg, potassium chloride 0.261 kg, calcium chloride hydrate 0.386 kg, magnesium chloride hydrate 0.178 kg, and anhydrous sodium acetate 0.144 kg were mixed under heating, and after further addition of water 0.178 kg, the mixture was granulated and dried at 130° C. to obtain an electrolyte composition. Then, the electrolyte composition 238.2 g, sodium diacetate 9.95 g, and glucose 52.5 g were mixed with stirring to obtain a dialysis agent A. The molar ratio of acetic acid:sodium acetate in the obtained dialysis agent A is 1:1.5.

Example 4

First, sodium chloride 10.84 kg, potassium chloride 0.261 kg, calcium chloride hydrate 0.386 kg, and magnesium chloride hydrate 0.178 kg were mixed under heating, and after further addition of water 0.178 kg, the mixture was granulated and dried at 130° C. to obtain an electrolyte composition. Then, the electrolyte composition 233.3 g, sodium diacetate 9.95 g, anhydrous sodium acetate 5.74 g, and glucose 52.5 g were mixed with stirring to obtain a dialysis agent A. The molar ratio of acetic acid:sodium acetate in the obtained dialysis agent A is 1:2.

Example 5

First, sodium chloride 10.99 kg, potassium chloride 0.261 kg, calcium chloride hydrate 0.386 kg, magnesium chloride hydrate 0.178 kg, and sodium lactate (70%) 0.140 kg were mixed under heating, and after further addition of water 0.178 kg, the mixture was granulated and dried at 130° C. to obtain an electrolyte composition. Then, the electrolyte composition 238.3 g, sodium diacetate 9.95 g, and glucose 52.5 g were mixed with stirring to obtain a dialysis agent A. The molar ratio of acetic acid:sodium acetate in the obtained dialysis agent A is 1:1.

Example 6

First, sodium chloride 11.10 kg, potassium chloride 0.261 kg, calcium chloride hydrate 0.386 kg, magnesium chloride hydrate 0.178 kg, and anhydrous sodium acetate 0.072 kg were mixed under heating, and after further addition of water 0.178 kg, the mixture was granulated and dried at 130° C. to obtain an electrolyte composition. Then, the electrolyte composition 239.9 g, sodium diacetate 4.97 g, anhydrous citric acid 2.24 g, and glucose 52.5 g were mixed with stirring to obtain a dialysis agent A. The molar ratio of acetic acid:sodium acetate in the obtained dialysis agent A is 1:1.5.

Comparative Example 1

First, sodium chloride 11.25 kg, potassium chloride 0.261 kg, calcium chloride hydrate 0.386 kg, and magnesium chloride hydrate 0.178 kg were mixed under heating, and after further addition of water 0.178 kg, the mixture was granulated and dried at 130° C. to obtain an electrolyte composition. Then, the electrolyte composition 241.5 g, glacial acetic acid 4.20 g, and glucose 52.5 g were mixed with stirring to obtain a dialysis agent A. The molar ratio of acetic acid:sodium acetate in the obtained dialysis agent A is 1:0.

Comparative Example 2

First, sodium chloride 10.64 kg, potassium chloride 0.261 kg, calcium chloride hydrate 0.386 kg, magnesium chloride hydrate 0.178 kg, and anhydrous sodium acetate 0.574 kg were mixed under heating, and after further addition of water 0.178 kg, the mixture was granulated and dried at 130° C. to obtain an electrolyte composition. Then, the electrolyte composition 240.7 g, glacial acetic acid 4.20 g, anhydrous sodium acetate 5.74 g, and glucose 52.5 g were mixed with stirring to obtain a dialysis agent A. The acetic acid:sodium acetate molar ratio in the obtained dialysis agent A is 1:3.

For each dialysis agent A (Comparative Examples 1 and 2, and Examples 1 to 6), the kind and amount of components added as acetic acid and/or acetate salt, and the molar ratio of acetic acid:sodium acetate are shown in Table 3.

TABLE 3

| | Kind and amount of components added as acetic acid and/or acetate salt | | | | Acetic acid:sodium acetate molar ratio |
|---|---|---|---|---|---|
| | Sodium acetate granules[#1] (g) | Sodium diacetate[#2] (g) | Acetic acid[#3] (g) | Sodium acetate[#4] (g) | |
| Comparative Example 1 | 0 | 0 | 4.20 | 0 | 1:0 |
| Example 1 | 0 | 4.97 | 2.10 | 0 | 1:0.5 |
| Example 2 | 0 | 9.95 | 0 | 0 | 1:1 |
| Example 3 | 2.88 | 9.95 | 0 | 0 | 1:1.5 |
| Example 4 | 0 | 9.95 | 0 | 5.74 | 1:2 |
| Comparative Example 2 | 11.48 | 0 | 4.20 | 5.74 | 1:3 |
| Example 5 | 0 (Sodium lactate 1.96 g was added) | 9.95 | 0 | 0 | 1:1 |
| Example 6 | 1.44 | 4.97 | 0 (Citric acid 2.24 g was added) | 0 | 1:1.5 |

[#1] "Sodium acetate granules" are powdered anhydrous sodium acetate that is not in the form of sodium diacetate (a commercially available product) (distributor: Wako Pure Chemical Industries, Ltd.)
[#2] "Sodium diacetate" is a commercially available sodium diacetate (distributor: Wako Pure Chemical Industries, Ltd.)
[#3] "Acetic acid" is a commercially available glacial acetic acid that is not in the form of sodium diacetate (distributor: Wako Pure Chemical Industries, Ltd.).
[#4] "Sodium acetate" is powdered anhydrous sodium acetate (a commercially available product) that is not in the form of sodium diacetate (distributor: Wako Pure Chemical Industries, Ltd.).

(2) Evaluation of Dialysis Agent A (Volatilized Acetic Acid Concentration and Moisture Content of Dialysis Agent A)

The concentration of volatilized acetic acid of each dialysis agent A obtained above was measured in the following manner. Each dialysis agent A in a predetermined amount shown in Table 4 was accommodated in a silica vapor deposition laminated bag, and a detector tube was set over the dialysis agent A, and a fixed amount of a gaseous sample was passed through the detector tube so that the concentration of volatilized acetic acid was measured by a detector tube type gas measuring instrument (manufacturer: GASTEC CORPORATION, model number: GV-100S).

Further, for each dialysis agent A of Examples 2 to 4, the moisture content was measured using a Karl Fischer moisture meter (manufacturer: Hiranuma Sangyo Co., Ltd., model number: AVQ-6)

(pH and 5-HMF Amount of 35-Fold Concentrated Agent A Solution)

Further, a 35-fold concentrated agent A solution was prepared by dissolving in purified water each dialysis agent A obtained above to an aqueous solution state wherein such an agent A was concentrated to 35 times the concentration of each component in the finally prepared dialysis fluid. Specifically, the 35-fold concentrated agent A solution was prepared by dissolving in purified water a predetermined amount shown in Table 4 of each dialysis agent A to a volume of 500 mL.

TABLE 4

| Solid dialysis agent A used | Amount of dialysis agent A subjected to measurement of volatilized acetic acid concentration and moisture content (g), and amount of dialysis agent A dissolved in purified water (g) |
|---|---|
| Comparative Example 1 | 149.1 |
| Example 1 | 149.5 |
| Example 2 | 149.9 |
| Example 3 | 150.3 |
| Example 4 | 150.8 |

TABLE 4-continued

| Solid dialysis agent A used | Amount of dialysis agent A subjected to measurement of volatilized acetic acid concentration and moisture content (g), and amount of dialysis agent A dissolved in purified water (g) |
|---|---|
| Comparative Example 2 | 151.6 |
| Example 5 | 150.4 |
| Example 6 | 149.8 |

The pH of the obtained 35-fold concentrated agent A solution and the amount of 5-hydroxymethylfurfural (hereinafter referred to as 5-HMF) that is the degradation product of glucose were measured. The pH was measured using a pH meter (manufacturer: Horiba, Ltd.; model number: F-73) at a liquid temperature of 25° C. With respect to the amount of 5-HMF, the absorbance of 5-HMF at the absorption wavelength (wavelength 284 nm) on the filtrate obtained by filtration with a 0.2 μm filter was measured using a spectrophotometer.

In addition, a bicarbonate dialysis fluid was prepared by accurately weighing 10 mL of the 35-fold concentrated agent A solution after the preparation, adding purified water thereto to a volume of 300 ml, adding a dialysis agent B (sodium hydrogen carbonate) 0.94 g to the mixture (the bicarbonate ion concentration in the dialysis fluid was 32 mEq/L), and adding purified water thereto to make a volume of 350 ml accurately. All of the obtained bicarbonate dialysis fluids (the dialysis agents A of Examples 1 to 6 and Comparative Examples 1 to 2 were used.) contain sodium ions of 140 mEq/L, potassium ions of 2 mEq/L, calcium ions of 3 mEq/L, and magnesium ions of 1 mEq/L.

The pH and the ionized calcium concentration of the bicarbonate dialysis fluid obtained were measured. The pH was measured using a pH meter (manufacturer: Horiba, Ltd.; model number: F-73) at a liquid temperature of 25° C. and the ionized calcium concentration was measured using a blood gas analyzer cobas b121 (manufacturer: Roche Diagnostics).

(Results)

The measurement results of the volatilized acetic acid concentration and the moisture content of the dialysis agent A, as well as the measurement results of the pH and the amount of 5-HMF (absorbance at 284 nm) of the 35-fold concentrated agent A solution are shown in Table 5. Also, the measurement results of the concentration of total acetate ions contained, the pH, and the ionized calcium concentration of each bicarbonate dialysis fluid obtained are shown in Table 6.

In the 35-fold concentrated agent A solution prepared from the dialysis agent A (Comparative Example 1) having the molar ratio of acetic acid:acetate salt of 1:0, it had a low pH of about 2.6, was strongly acidic, failed to exhibit a sufficient safety for handling, and was such a formulation that raises concern for corrosion of the dialysis fluid preparation apparatus and the dialysis machine. Further, in the dialysis agent A of Comparative Example 1, the volatilized acetic acid concentration exceeded 1000 ppm, which was an unacceptable level in the clinical practice. In addition, the absorbance at 284 nm, which is the absorption wavelength of 5-HMF, was already higher than that in other Examples after the preparation, and glucose was not able to be stably maintained. Moreover, in spite of the molar ratio of acetic acid:acetate salt molar of 1:3 in the dialysis agent A of Comparative Example 2 in which sodium diacetate was not contained, the volatilized acetic acid concentration was a high value of 900 ppm.

In contrast, the 35-fold concentrated agent A solution prepared from the dialysis agent A (Examples 1 to 6) containing sodium diacetate and having the molar ratio of acetic acid:acetate salt within a range of 1:0.5 to 2 showed a pH of 3.9 or more, which can be handled safely in the clinical practice and will not cause the corrosion of the dialysis fluid preparation apparatus and the dialysis machine. Also, the 35-fold concentrated agent A solution prepared from the dialysis agent A (Examples 1 to 6) showed a low value of the absorbance at a wavelength of 284 nm, which is the absorption wavelength of 5-HMF, after preparation as compared to Comparative Example 1, and thus glucose degradation was sufficiently suppressed. Further, in the dialysis agent A of each of Examples 1 to 6, the volatilized acetic acid concentration was lower than that of each of Comparative Examples 1 and 2. In particular, Examples 2 to 6 (acetic acid:acetate salt=1:1 to 2)) showed significantly lower values of the absorbance at a wavelength of 284 nm and the volatilized acetic acid concentration.

Further, the bicarbonate dialysis fluid prepared by using the dialysis agent A of each of Examples 1 to 6 had a total acetate ion concentration of 2 mEq/L or higher but less than 6 mEq/L and maintained a suitable pH as a dialysis fluid. The ionized calcium concentration was low in Example 6 due to the chelating action of the citric acid contained, but such ionized calcium concentration was maintained at a sufficiently high level in Examples 1 to 5.

TABLE 5

|  | Acetic acid:sodium acetate molar ratio | Volatilized acetic acid concentration of dialysis agent A (ppm) | Moisture content of dialysis agent A (wt %) | pH of 35-fold concentrated agent A solution | Absorbance of 35-fold concentrated agent A solution (284 nm) |
| --- | --- | --- | --- | --- | --- |
| Comparative Example 1 | 1:0 | >1000 | Not measured | 2.65 | 0.0065 |
| Example 1 | 1:0.5 | 650 | Not measured | 4.03 | 0.0059 |
| Example 2 | 1:1 | 20 | 0.62 | 4.31 | 0.0049 |
| Example 3 | 1:1.5 | 15 | 0.59 | 4.51 | 0.0039 |
| Example 4 | 1:2 | 10 | 0.61 | 4.63 | 0.0035 |
| Comparative Example 2 | 1:3 | 900 | Not measured | 4.79 | 0.0021 |
| Example 5 | 1:1 | 10 | Not measured | 4.31 | 0.0053 |
| Example 6 | 1:1.5 | 5 | Not measured | 3.93 | 0.0040 |

TABLE 6

|  |  | Bicarbonate dialysis fluid | | |
| --- | --- | --- | --- | --- |
|  | Molar ratio of acetic acid:sodium acetate in dialysis agent A used | Total acetate ion concentration (mEq/L) | pH | Ionized calcium concentration (mmol/L) |
| Comparative Example 1 | 1:0 | 2 | 7.40 | 1.48 |
| Example 1 | 1:0.5 | 3 | 7.41 | 1.44 |
| Example 2 | 1:1 | 4 | 7.40 | 1.42 |
| Example 3 | 1:1.5 | 5 | 7.41 | 1.40 |
| Example 4 | 1:2 | 5.997 | 7.40 | 1.38 |
| Comparative Example 2 | 1:3 | 8 | 7.39 | 1.34 |
| Example 5 | 1:1 | 4 | 7.39 | 1.42 |
| Example 6 | 1:1.5 | 2.5 | 7.39 | 1.22 |

(3) Evaluation of Long Term Stability of Dialysis Agent A

A predetermined amount shown in Table 7 of each dialysis agent A (Examples 1 to 6 and Comparative Examples 1 to 2) was accommodated in a polyethylene bag. Furthermore, this was accommodated in a packaging bag shown in Table 8, sealed, and stored for 2 months at 25° C. and 60% RH.

TABLE 7

| Solid dialysis agent A used | Amount (g) of solid dialysis agent A accommodated in packaging bag and amount (g) of dialysis agent A dissolved in purified water |
|---|---|
| Comparative Example 1 | 149.1 |
| Example 1 | 149.5 |
| Example 2 | 149.9 |
| Example 3 | 150.3 |
| Example 4 | 150.8 |
| Comparative Example 2 | 151.6 |
| Example 5 | 150.4 |
| Example 6 | 149.8 |

TABLE 8

| Notation of packaging bag | Composition of packaging bag |
|---|---|
| PET/AL/PE bag | A laminated bag (water vapor transmission is substantially 0 g/m$^2$ · 24 h) made of a laminate wherein a polyethylene terephthalate film, an aluminum foil, and a polyethylene film are laminated. |
| PET/AL/PE bag + Zeolite (1%) | The PET/AL/PE bag in which 1 part by weight of zeolite is added as a desiccant, per 100 parts by weight of a dialysis agent A to be accommodated therein. |

Before storage, after two weeks storage, after one month storage, and after two months storage, a detector tube was set in a polyethylene bag in which each dialysis agent A had been accommodated, and a fixed amount of a gaseous sample was passed through the detector tube for measuring acetic acid, so that the volatilized acetic acid concentration was measured by a gas detector tube type gas measuring instrument (manufacturer: GASTEC CORPORATION, model number: GV-100S).

Further, a 35-fold concentrated agent A solution was prepared by dissolving in purified water each fixed amount shown in Table 4 of each dialysis agent A after two weeks storage, after one month storage, and after two months storage, to a volume of 500 mL wherein the agent A was concentrated to 35 times the concentration of each component in the finally prepared dialysis fluid. The amount of 5-HMF of the 35-fold concentrated agent A solution obtained was measured in the same manner as above.

The results of measuring the volatilized acetic acid concentration in the dialysis agent A before and after storage are shown in Table 9, and the results of measuring the amount of 5-HMF of the 35-fold concentrated agent A solution prepared by using the dialysis agent A before and after storage are shown in Table 10.

As a result, the volatilized acetic acid concentration and the amount of 5-HMF were high in the dialysis agent A of Comparative Example 1 before storage, and the volatilization of acetic acid as well as the degradation of glucose was not suppressed. Further, also in Comparative Example 2, the volatilized acetic acid concentration before storage was high, which is unacceptable in the clinical practice. On the other hand, each dialysis agent A of Examples 2 to 6 was able to sufficiently suppress the volatilization of acetic acid and the degradation of glucose even after 2 months storage. Further, from the test results, it was revealed that the volatilization of acetic acid and the degradation of glucose can be more effectively suppressed by adding a desiccant in a package for storing the dialysis agent A.

TABLE 9

Measurement results of volatilized acetic acid concentration (ppm)

| | Before storage | After two weeks | | After one month | | After two months | |
|---|---|---|---|---|---|---|---|
| | | PET/AL/PE bag | PET/AL/PE bag + zeolite (1%) | PET/AL/PE bag | PET/AL/PE bag + zeolite (1%) | PET/AL/PE bag | PET/AL/PE bag + zeolite (1%) |
| Comparative Example 1 | >1000 | >1000 | >1000 | >1000 | >1000 | >1000 | >1000 |
| Example 1 | 650 | Not measured | Not measured | Not measured | Not measured | Not measured | Not measured |
| Example 2 | 20 | 20 | 10 | 30 | 20 | 40 | 40 |
| Example 3 | 15 | 15 | 10 | 40 | 20 | 35 | 40 |
| Example 4 | 10 | 15 | 10 | 45 | 15 | 40 | 30 |
| Comparative Example 2 | 900 | 200 | 120 | 250 | 200 | 200 | 200 |
| Example 5 | 10 | 5 | 10 | 50 | 30 | 40 | Not measured |
| Example 6 | 5 | 5 | 5 | 35 | 25 | 35 | 35 |

TABLE 10

Measurement results of 5-HMF (absorbance: 284 nm)

| | Before storage | After two weeks | | After one month | | After two months | |
|---|---|---|---|---|---|---|---|
| | | PET/AL/PE bag | PET/AL/PE bag + zeolite (1%) | PET/AL/PE bag | PET/AL/PE bag + zeolite (1%) | PET/AL/PE bag | PET/AL/PE bag + zeolite (1%) |
| Comparative Example 1 | 0.0065 | 0.0242 | 0.0212 | 0.0512 | 0.0404 | 0.1231 | 0.1084 |
| Example 1 | 0.0059 | Not measured | Not measured | Not measured | Not measured | Not measured | Not measured |
| Example 2 | 0.0049 | 0.0045 | 0.0042 | 0.0037 | 0.0038 | 0.0055 | 0.0052 |
| Example 3 | 0.0039 | 0.0047 | 0.0045 | 0.0042 | 0.0038 | 0.0053 | 0.0053 |

TABLE 10-continued

Measurement results of 5-HMF (absorbance: 284 nm)

|  | Before storage | After two weeks | | After one month | | After two months | |
|---|---|---|---|---|---|---|---|
|  |  | PET/AL/PE bag | PET/AL/PE bag + zeolite (1%) | PET/AL/PE bag | PET/AL/PE bag + zeolite (1%) | PET/AL/PE bag | PET/AL/PE bag + zeolite (1%) |
| Example 4 | 0.0035 | 0.0043 | 0.0041 | 0.0042 | 0.0037 | 0.0048 | 0.0052 |
| Comparative Example 2 | 0.0021 | 0.0056 | 0.0035 | 0.0091 | 0.0031 | 0.0090 | 0.0053 |
| Example 5 | 0.0053 | 0.0059 | 0.0060 | 0.0058 | 0.0057 | 0.0063 | Not measured |
| Example 6 | 0.0040 | 0.0048 | 0.0047 | 0.0049 | 0.0040 | 0.0053 | 0.0056 |

Test Example 2

(1) Preparation of Dialysis Agent A

Example 7

First, sodium chloride 11.05 kg, potassium chloride 0.261 kg, calcium chloride hydrate 0.386 kg, and magnesium chloride hydrate 0.178 kg were mixed under heating, and after further addition of water 0.178 kg, the mixture was granulated and dried at 130° C. to obtain an electrolyte composition. Then, the electrolyte composition 237.4 g, sodium diacetate 9.95 g, and glucose 52.5 g were mixed with stirring to obtain a dialysis agent A. The molar ratio of acetic acid:sodium acetate in the obtained dialysis agent A is 1:1.

Example 8

First, sodium chloride 11.05 kg, potassium chloride 0.261 kg, calcium chloride hydrate 0.386 kg, and magnesium chloride hydrate 0.178 kg were mixed under heating, and after further addition of water 0.178 kg, the mixture was granulated and dried at 130° C. to obtain an electrolyte composition. Further, separately, glacial acetic acid 0.105 kg and anhydrous sodium acetate 0.144 kg were mixed to obtain an acetic acid/sodium acetate mixture. The electrolyte composition 237.4 g, sodium diacetate 6.96 g, the acetic acid/sodium acetate mixture 2.98 g, and glucose 52.5 g were mixed with stirring to obtain a dialysis agent A. The molar ratio of acetic acid:sodium acetate in the obtained dialysis agent A is 1:1.

Example 9

First, sodium chloride 11.05 kg, potassium chloride 0.261 kg, calcium chloride hydrate 0.386 kg, and magnesium chloride hydrate 0.178 kg were mixed under heating, and after further addition of water 0.178 kg, the mixture was granulated and dried at 130° C. to obtain an electrolyte composition. Further, separately, glacial acetic acid 0.105 kg and anhydrous sodium acetate 0.144 kg were mixed to obtain an acetic acid/sodium acetate mixture. The electrolyte composition 237.4 g, sodium diacetate 4.97 g, the acetic acid/sodium acetate mixture 4.97 g, and glucose 52.5 g were mixed with stirring to obtain a dialysis agent A. The molar ratio of acetic acid:sodium acetate in the obtained dialysis agent A is 1:1.

Example 10

First, sodium chloride 11.05 kg, potassium chloride 0.261 kg, calcium chloride hydrate 0.386 kg, and magnesium chloride hydrate 0.178 kg were mixed under heating, and after further addition of water 0.178 kg, the mixture was granulated and dried at 130° C. to obtain an electrolyte composition. Further, separately, glacial acetic acid 0.105 kg and anhydrous sodium acetate 0.144 kg were mixed to obtain an acetic acid/sodium acetate mixture. The electrolyte composition 237.4 g, sodium diacetate 1.99 g, the acetic acid/sodium acetate mixture 7.96 g, and glucose 52.5 g were mixed with stirring to obtain a dialysis agent A. The molar ratio of acetic acid:sodium acetate in the obtained dialysis agent A is 1:1.

For each dialysis agent A (Examples 7 to 10), the kind and amount of the components added as acetic acid and/or sodium acetate, and the molar ratio of acetic acid:sodium acetate are shown in Table 11.

TABLE 11

| | Kind and amount of components added as acetic acid and/or acetate salt | | | |
|---|---|---|---|---|
| | | Components in acetic acid/sodium acetate mixture | | Acetic acid:sodium acetate molar ratio |
| | Sodium diacetate[1] (g) | Acetic acid[2] (g) | Sodium acetate[3] (g) | |
| Example 7 | 9.95 | 0 | 0 | 1:1 |
| Example 8 | 6.96 | 1.26 | 1.72 | 1:1 |
| Example 9 | 4.97 | 2.10 | 2.87 | 1:1 |
| Example 10 | 1.99 | 3.36 | 4.59 | 1:1 |

[1]"Sodium diacetate" is a commercially available sodium diacetate (distributor: Wako Pure Chemical Industries, Ltd.)
[2]"Acetic acid" is a commercially available glacial acetic acid that is not in the form of sodium diacetate (distributor: Wako Pure Chemical Industries, Ltd.).
[3]"Sodium acetate" is a commercially available powdered sodium acetate that is not in the form of sodium diacetate (distributor: Wako Pure Chemical Industries, Ltd.).

(2) Evaluation of Long Term Stability of Dialysis Agent A

Each dialysis agent A (Examples 7 to 10) 149.9 g was respectively accommodated in a polyethylene bag. Furthermore, this was accommodated in a PET/AL/PE bag shown in Table 8, sealed, and stored for 2 months at 25° C. and 60% RH.

The volatilized acetic acid concentration of each of dialysis agents A before storage, after two weeks storage, after one month storage, and after two months storage was measured in the same manner as in Test Example 1. Further, a 35-fold concentrated agent A solution was prepared by dissolving in purified water 149.9 g of each of dialysis agents A before storage, after two weeks storage, after one month storage, and after two months storage to a volume of 500 mL wherein the agent A was concentrated to 35 times the concentration of each component in the finally prepared dialysis fluid. The pH and the amount of 5-HMF of the resulting 35-fold concentrated agent A solution were measured in the same manner as in Test Example 1.

The results obtained are shown in Tables 12 and 13. From the results shown in Tables 12 and 13, the dialysis agents A of Examples 7 to 10 sufficiently suppressed the volatilization of acetic acid and the degradation of glucose even after two months storage, and thus they were excellent in storage stability.

TABLE 12

| | Volatilized acetic acid concentration (ppm) | | | |
|---|---|---|---|---|
| | Before storage | After two weeks storage | After one month storage | After two months storage |
| Example 7 | 20 | 20 | 30 | 40 |
| Example 8 | 20 | 20 | 20 | 40 |
| Example 9 | 10 | 10 | 20 | 40 |
| Example 10 | 10 | 10 | 20 | 40 |

TABLE 13

| | pH of 35-fold concentrated agent A solution Before storage | 5-HMF (absorbance: 284 nm) | | |
|---|---|---|---|---|
| | | Before storage | After two weeks storage | After one month storage | After two months storage |
| Example 7 | 4.31 | 0.0037 | 0.0043 | 0.0037 | 0.0055 |
| Example 8 | 4.30 | 0.0036 | 0.0052 | 0.0049 | 0.0056 |
| Example 9 | 4.30 | 0.0031 | 0.0046 | 0.0035 | 0.0054 |
| Example 10 | 4.30 | 0.0027 | 0.0036 | 0.0040 | 0.0045 |

Test Example 3

(1) Preparation of Dialysis Agent A

Example 11

First, sodium chloride 10.99 kg, potassium chloride 0.261 kg, calcium chloride hydrate 0.386 kg, magnesium chloride hydrate 0.178 kg, and anhydrous sodium acetate 0.072 kg were mixed under heating, and after further addition of water 0.178 kg, the mixture was granulated and dried at 130° C. while changing the drying time to obtain an electrolyte composition with a different moisture content. The electrolyte composition 237.8 g, sodium diacetate 9.95 g, and glucose 52.5 g were mixed with stirring to obtain a dialysis agent A. The moisture content of the dialysis agent A obtained by this procedure was measured using a Karl Fischer moisture meter (manufacturer: Hiranuma Sangyo Co., Ltd., model number: AVQ-6) to find that the moisture content was 1.0% by weight (Example 11-1), 1.1% by weight (Example 11-2), and 1.3% by weight (Example 11-3). Further, molar ratio of the acetic acid:sodium acetate in the obtained dialysis agent A is 1:1.25.

(2) Evaluation of Dialysis Agent A

With respect to each dialysis agent A obtained above, the volatilized acetic acid concentration was measured in the same manner as in Test Example 1 mentioned above.

The results obtained are shown in Table 14. As can be clearly seen from Table 14, when the moisture content of the dialysis agent A was 1.1% by weight or less, the dialysis agent A showed a low value of 100 ppm or less of the volatilized acetic acid concentration, and thus a particularly remarkable effect of reducing the acetic acid odor was observed.

TABLE 14

| | Moisture content (% by weight) | Volatilized acetic acid concentration (ppm) |
|---|---|---|
| Example 11-1 | 1.0 | 15 |
| Example 11-2 | 1.1 | 100 |
| Example 11-3 | 1.3 | 400 |

Test Example 4

(1) Preparation of Dialysis Agent A

Example 12-1

First, sodium chloride 11.05 kg, potassium chloride 0.261 kg, calcium chloride hydrate 0.386 kg, and magnesium chloride hydrate 0.178 kg were mixed under heating, and after further addition of water 0.178 kg, the mixture was granulated and dried at 130° C. to obtain an electrolyte composition. Then, the electrolyte composition 237.4 g, sodium diacetate 9.95 g, and glucose 52.5 g were mixed with stirring to obtain a dialysis agent A. The molar ratio of acetic acid:sodium acetate in the obtained dialysis agent A is 1:1.

Example 12-2

Sodium chloride 220.90 g, potassium chloride 5.22 g, anhydrous calcium chloride 5.83 g, anhydrous magnesium chloride 1.67 g, sodium diacetate 9.95 g, and glucose 52.5 g were simply mixed to obtain a dialysis agent A. The molar ratio of acetic acid:sodium acetate in the obtained dialysis agent A is 1:1.

Example 13-1

First, sodium chloride 10.94 kg, potassium chloride 0.261 kg, calcium chloride hydrate 0.386 kg, magnesium chloride hydrate 0.178 kg, and anhydrous sodium acetate 0.144 kg were mixed under heating and after further addition of water 0.178 kg, the mixture was granulated and dried at 130° C. to obtain an electrolyte composition. Then, the electrolyte composition 238.2 g, sodium diacetate 9.95 g, and glucose 52.5 g were mixed with stirring to obtain a dialysis agent A. The molar ratio of acetic acid:sodium acetate in the obtained dialysis agent A is 1:1.5.

Example 13-2

Sodium chloride 218.86 g, potassium chloride 5.22 g, anhydrous calcium chloride 5.83 g, anhydrous magnesium chloride 1.67 g, anhydrous sodium acetate 2.87 g, sodium diacetate 9.95 g, and glucose 52.5 g were simply mixed to obtain a dialysis agent A. The molar ratio of acetic acid: sodium acetate in the obtained dialysis agent A is 1:1.5.

Example 14

Sodium chloride 220.90 g, potassium chloride 5.22 g, calcium chloride hydrate 7.72 g, magnesium chloride hydrate 3.56 g, sodium diacetate 9.95 g, and glucose 52.5 g were simply mixed to obtain a dialysis agent A. The molar ratio of acetic acid:sodium acetate in the obtained dialysis agent A is 1:1.

Example 15

Sodium chloride 218.86 g, potassium chloride 5.22 g, calcium chloride hydrate 7.72 g, magnesium chloride hydrate 3.56 g, anhydrous sodium acetate 2.87 g, sodium diacetate 9.95 g, and glucose 52.5 g were simply mixed to obtain a dialysis agent A. The molar ratio of acetic acid:sodium acetate in the obtained dialysis agent A is 1:1.5.

(2) Evaluation of Dialysis Agent A (Moisture Content of Dialysis Agent A)
The moisture content of each dialysis agent A obtained above was measured using a Karl Fischer moisture meter (manufacturer: Hiranuma Sangyo Co., Ltd., model number: AVQ-6) (The average value was calculated in n=2.)
(Measurement of Volatilized Acetic Acid Concentration of Dialysis Agent A After Storage and 5-HMF of 35-Fold Concentrated Agent A Solution)
Each dialysis agent A in a predetermined amount shown in Table 15 was accommodated in a polyethylene bag, and this was further accommodated in a PET/AL/PE bag, sealed, and stored for 2 weeks at 40° C. and 75% RH.
Before storage and after two weeks storage of each dialysis agent A, a detector tube was set in a polyethylene bag in which the each dialysis agent A had been accommodated and a fixed amount of a gaseous sample was passed through the detector tube for measuring acetic acid so that the concentration of volatilized acetic acid was measured by a gas detector tube type gas measuring instrument (manufacturer: GASTEC CORPORATION, model number: GV-100S).
Further, the amount of 5-HMF of the 35-fold concentrated agent A solution was measured in the same manner as in Test Example 1. The 35-fold concentrated agent A solution was prepared by dissolving in purified water each of dialysis agents A before storage and after two weeks storage in a predetermined amount shown in Table 15 to a volume of 500 mL wherein the agent A was concentrated to 35 times the concentration of each component in the finally prepared dialysis fluid. In addition, the pH of the 35-fold concentrated agent A solution prepared by using the dialysis agent A after the preparation was measured in the same manner as in Test Example 1 mentioned above.

TABLE 15

| Dialysis agent A used | Amount (g) of dialysis agent A subjected to measurement of volatilized acetic acid concentration and moisture content, and amount (g) of dialysis agent A dissolved in purified water (g) |
|---|---|
| Example 14 | 149.9 |
| Example 12-1 | 149.9 |
| Example 12-2 | 148.0 |
| Example 15 | 150.3 |
| Example 13-1 | 150.3 |
| Example 13-2 | 148.4 |

The results of measurement for moisture content of the dialysis agent A are shown in Table 16. Also, the results of measuring the volatilized acetic acid concentration in the dialysis agent A before and after the storage as well as the results of measuring the pH and 5-HMF amount of the 35-fold concentrated agent A solution prepared by using the dialysis agent A before and after the storage are shown in Table 17. In the dialysis agent A of Examples 14 and 15 obtained by using calcium chloride and magnesium chloride as hydrates, followed by simple mixing, the moisture content was 1.5% by weight, while in Examples 12-1 and 13-1 wherein calcium chloride hydrate and magnesium chloride hydrate were used, mixed, and subjected to drying treatment as well as in Examples 12-2 and 13-2 wherein anhydrous calcium chloride and anhydrous magnesium chloride were used, the moisture content was reduced to less than 0.7% by weight. It was confirmed from Table 17 that in all of the dialysis agents A of Examples 12 to 15, stable dialysis agents A was produced because the volatilized acetic acid concentration and the 5-HMF amount were low before the storage. In addition, in Examples 12-1, 12-2, 13-1, and 13-2 wherein the moisture content was low, the amount of the volatilized acetic acid was kept low and the degradation of glucose was effectively inhibited, whereas in Examples 14 and 15 wherein the moisture content was about 1.5% by weight, the amounts of the volatilized acetic acid and 5-HMF were not suppressed. When the dialysis agent A was stored at a more severe environment of 40° C. and 75% RH compared to Test Examples described earlier, a significant influence of the moisture on the stability of the dialysis agent A was observed. From the above results, it was found that, in order to produce a more stable dialysis agent A, it is preferable to reduce the moisture content of the dialysis agent A by performing the drying process or the like.

TABLE 16

| Dialysis agent A used | Molar ratio of acetic acid:sodium acetate in dialysis agent A | Moisture content in dialysis agent A (% by weight) |
|---|---|---|
| Example 14 | 1:1 | 1.54 |
| Example 12-1 | 1:1 | 0.66 |
| Example 12-2 | 1:1 | 0.44 |
| Example 15 | 1:1.5 | 1.49 |
| Example 13-1 | 1:1.5 | 0.60 |
| Example 13-2 | 1:1.5 | 0.45 |

TABLE 17

| | pH of 35-fold concentrated agent A solution | Volatilized acetic acid concentration (ppm) | | 5-HMF (absorbance: 284 nm) | |
|---|---|---|---|---|---|
| | | Before storage | After two weeks storage | Before storage | After two weeks storage |
| Example 14 | 4.28 | 80 | >1000 | 0.0032 | 0.1459 |
| Example 12-1 | 4.31 | 30 | 80 | 0.0043 | 0.0054 |
| Example 12-2 | 4.28 | 30 | 20 | 0.0035 | 0.0039 |
| Example 15 | 4.47 | 60 | >1000 | 0.0028 | 0.1616 |
| Example 13-1 | 4.50 | 50 | 90 | 0.0043 | 0.0053 |
| Example 13-2 | 4.47 | 50 | 10 | 0.0031 | 0.0042 |

The invention claimed is:
1. A solid dialysis agent A configured to be used in the preparation of a bicarbonate dialysis fluid, wherein:
the solid dialysis agent A comprises glucose, acetic acid, and an acetate salt, wherein at least a part of a mixture of the acetic acid with the acetate salt is an alkali metal diacetate,
the molar ratio of acetic acid:acetate salt is 1:1.1 to 1.5,
the moisture content is 1.1% by weight or less, and wherein the solid dialysis agent A is to configured to be used for preparing a bicarbonate dialysis fluid having total acetate ions of 2 mEq/L or higher but less than 6 mEq/L.

2. The dialysis agent A according to claim 1, wherein the alkali metal diacetate is sodium diacetate and/or potassium diacetate.

3. The dialysis agent A according to claim 1, which is configured to be used for preparing a dialysis fluid having total acetate ions of 2 mEq/L or higher but 5 mEq/L or less.

4. The dialysis agent A according to claim 1, wherein when the dialysis agent A is converted into a state of an aqueous solution that is concentrated to 35 times the concentration of each component in the finally prepared dialysis fluid, the pH of the solution is 3.9 to 4.6.

5. The dialysis agent A according to claim 1, wherein the acetate salt is sodium acetate.

6. The dialysis agent A according to claim 1 further comprising a physiologically available electrolyte other than sources for acetic acid and an acetate salt.

7. The dialysis agent A according to claim 6, which comprises sodium chloride, potassium chloride, magnesium chloride, and calcium chloride as an electrolyte.

8. The dialysis agent A according to claim 6, which further comprises as the electrolyte an organic acid salt other than the acetate salt, and/or contains as a pH adjusting agent an organic acid salt and/or an organic acid other than the acetic acid and acetate salt.

9. The dialysis agent A according to claim 7, wherein the magnesium chloride and/or calcium chloride is a dried product or an anhydride.

10. The dialysis agent A according to claim 1, wherein the alkali metal diacetate is obtained by a reaction of acetic acid with an alkali metal acetate, an alkali metal hydroxide, an alkali metal carbonate, or an alkali metal bicarbonate.

11. The dialysis agent A according to claim 1, which comprises:
a first material comprising acetic acid and an acetate salt, wherein at least a part of a mixture of the acetic acid and acetate salt is an alkali metal diacetate, and a second material comprising a composition comprising a physiologically available electrolyte which is neither acetic acid nor acetate salt, wherein;
all of the acetic acid and acetate salt in the dialysis agent A are contained in the first material, or some of the acetic acid and acetate salt in the dialysis agent A are also contained in the second material, and
glucose is contained in the composition of the second material, and/or a third material comprising glucose separately from the first material and the second material is included.

12. The dialysis agent A according to claim 1, wherein the moisture content of the dialysis agent A is 1.0% by weight or less.

13. The dialysis agent A according to claim 1, which is accommodated in a packaging container of a water vapor transmission of 0.5 g/m$^2$·24 h or less.

14. The dialysis agent A according to claim 1, which is accommodated in a packaging container together with a desiccant.

15. A two-part type dialysis agent comprising the dialysis agent A according to claim 1 and a dialysis agent B containing sodium hydrogen carbonate.

16. A method for preparing a bicarbonate dialysis fluid, comprising the step of mixing the dialysis agent A according to claim 1 and a dialysis agent B containing sodium hydrogen carbonate with water in such an amount that the bicarbonate dialysis fluid has total acetate ions of 2 mEq/L or higher but less than 6 mEq/L.

* * * * *